Figure 1:
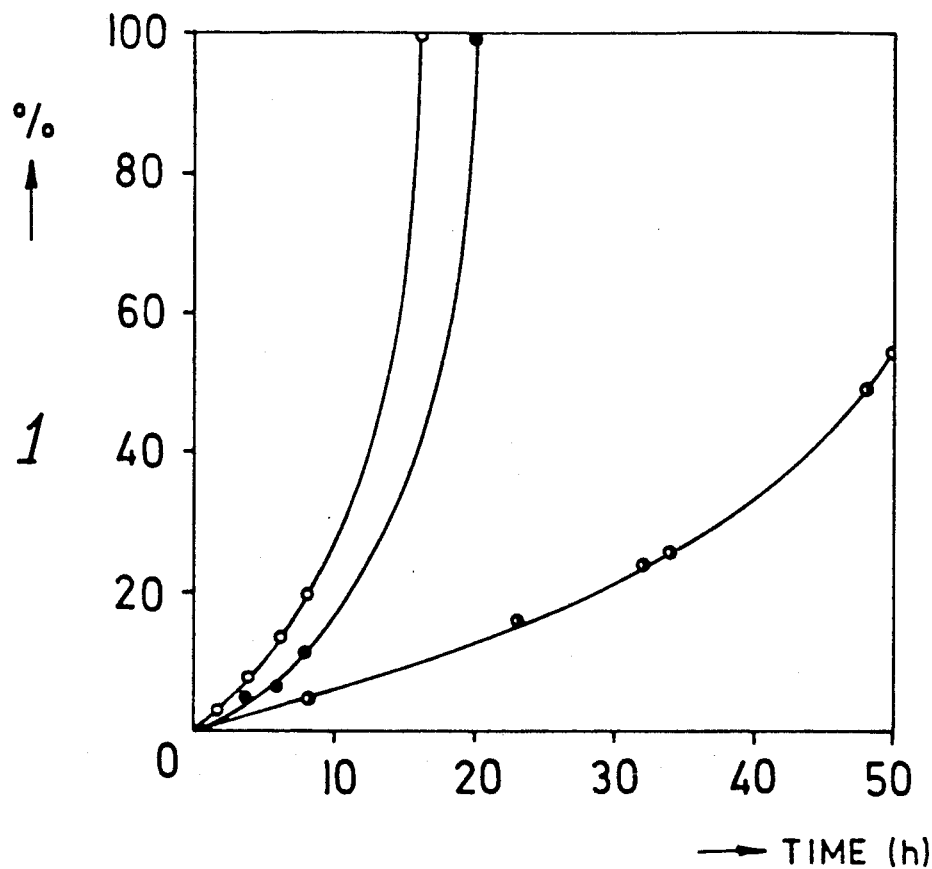

United States Patent [19]
Ulbrich et al.

[11] Patent Number: 5,124,421
[45] Date of Patent: Jun. 23, 1992

[54] HYDROLYTICALLY DEGRADABLE HYDROPHILIC GELS AND THE METHOD FOR PREPARATION THEREOF

[75] Inventors: Karel Ulbrich, Praha; Vladnír Šubr, Mělník, both of Czechoslovakia

[73] Assignee: Ceskoslovenska Akademie Ved, Praha, Czechoslovakia

[21] Appl. No.: 630,043

[22] Filed: Dec. 19, 1990

[30] Foreign Application Priority Data

Dec. 20, 1989 [CS] Czechoslovakia ............... 7222-89
Dec. 20, 1989 [CS] Czechoslovakia ............... 7223-89

[51] Int. Cl.⁵ .................... C08F 2/06; C08F 226/10
[52] U.S. Cl. .................... 526/212; 526/304; 526/263; 526/271; 526/220; 526/222; 524/916
[58] Field of Search .......... 526/212, 263, 271, 301, 526/302, 304; 524/916

[56] References Cited

PUBLICATIONS

Chem. Abstr. 101 (16): 131205x.
Chem. Abstr. 94: 42706.
J. Biomater. Sci Polymer Edn, vol. 3, No. 1, 2612–278 (1990) Subr V. Duncan R., Kopecek J. "Release of Macromolecules and Daunomycin from Hydrophilic Gels Containing Enzymatically Degradable Bonds. VI. Hydrophilic Gelscleavable by Chymotrypsin".
Makromol. Chem. 191, 1887–1897 (1990) Pradny M., Kopecek J. "Poly(acrylic Acid)-Co-(Butyl Acrylate) Crosslinked with 4,4-Bis(Methacryloylamino) Azobenzene".
Makromol. Chem. 178, 2515-2526 (1977) Braun D., Bredlein W., Jung Chul Jin "Vernetyte Polymers mit Spaltbaren Netzbrucken, Homopolymerisation vol. 4-Vinylbenzoesaureanhydrid".

Primary Examiner—Joseph L. Schofer
Assistant Examiner—M. Nagumo
Attorney, Agent, or Firm—Leydig, Voit & Mayer

[57] ABSTRACT

The solution pertains to hydrolytically degradable hydrophilic gels consisting of the individual chains of hydrophilic polymer interconnected with crosslinks containing the structure

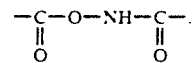

The method for preparation of the hydrolytically degradable gels consists in subjecting hydrophilic monomers or their mixture to the radical polymerization or copolymerization, or to copolymerization with hydrophobic monomers, in the presence of a new compound—N,O-dimethacryloylhydroxylamine—as a crosslinking agent, and, if desired, in the presence of a solvent, whereas the amount of hydrophilic monomers is 50 to 99.8 molar percent related to all monomers present.

9 Claims, 1 Drawing Sheet

HYDROLYTICALLY DEGRADABLE HYDROPHILIC GELS AND THE METHOD FOR PREPARATION THEREOF

The invention relates to hydrolytically degradable hydrophilic gels and the method of their preparation.

Hydrophilic gels can be defined as polymeric materials which are able to absorb even large amounts of water without dissolution. They found their use in many fields of medicine as implants, membranes for hemdialysis and ultrafiltration, non-thrombogenic surfaces of artificial organs, contact lenses and components of systems for the controlled drug release. The hydrophilic polymers concerned are connected into a threedimensional network by means of physical, ionic or covalent bonds. Although numerous hydrophilic gels are known, which are formed on the basis of ionic bonds and are hydrolytically cleavable, there is relatively few data on the hydrolytically cleavable gels with covalent crosslinks. The latter gels are, above all, the polymers containing ester bonds which dissolve after hydrolysis of these bonds (e.g. the copolymers of vinylpyrrolidone or polyethylene glycol with fumaric acid). The hydrolysis is pH-dependent and its rate is controlled both by the structure of ester bond vicinity and by the density of polymer network. Some other systems are based on hydrophilic synthetic polymers linked into a network with couplings formed from biomolecules (saccharides, peptides) which are cleavable with enzymes. The systems mentioned above are relatively poor defined and do not warrant reproducible results in the preparation. The system proposed by us is based on the preparation of a polymeric network by copolymerization of a monovinyl monomer with a precisely defined divinyl crosslinking agent containing a hydrolytically labile bond. In this way, gels can be prepared in a reproducible manner and the network density may be controlled not only by the content of solvent in polymerization mixture, but also by the ratio of both monomeric components at the same time with the rate of hydrolytic degradation of the gels strongly depends on their network density. Similar systems are not yet known.

An object of the present invention are hydrolytically degradable hydrophilic gels, which consist of individual chains of a hydrophilic polymer interconnected with crosslinks containing the structural unit

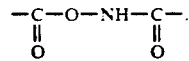

The basic feature of the hydrolytically degradable gels according to the invention is that the gels contain N, O-dimethacryloylhydroxylamine as the crosslinking agent.

The method for preparation of hydrolytically degradable hydrophilic gels according to the invention is based on the radical polymerization of hydrophilic monomers, or on their copolymerization with hydrophobic monomers, in the presence of N,O-dimethacryloylhydroxylamine as a crosslinking agent, or also in the presence of a solvent.

As the hydrophilic monomers for the preparation of hydrolytically degradable polymeric gels according to the invention, they can be advantageously used the monomers selected from the group comprising N-(2-hydroxypropyl)methacrylamide, N-isopropylacrylamide, N,N'-diethylacrylamide, N-ethylmethacrylamide, 2-hydroxyethyl methacrylate, 2-(2-hydroxyethoxy)ethyl methacrylate, acrylic acid, methacrylic acid, and others. The hydrophilic monomers can be used in the crosslinking homopolymerization in the amount of 90 to 99.8 weight percent of the polymerization mixture and, in the copolymerization with hydrophobic comonomers, in the amount of 50 to 99 molar percent related to all monomers in the polymerization mixture.

Suitable hydrophobic monomers can be selected from the 2-acetoxyethyl methacrylate, group of monomers comprising dimethylaminoethyl methacrylate, n-butyl methacrylate, tert-butylacrylamide, n-butyl acrylate, methyl methacrylate, and hexyl acrylate in the amount up to 50 molar percent related to all monomers present in the polymerization mixture.

The polymerization can be carried out in solvents, e.g., in dimethylsulfoxide, dimethylformamide, water, alcohols as methanol and ethanol, or in mixtures ethanol-water, using common initiators of the radical polymerization.

The hydrophilic gels crosslinked with N,O-dimethacryloylhydroxylamine, which are prepared in this way, contain the structure unit

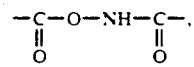

which is hydrolytically labile. The most important in the preparation of these gels is just this crosslinking agent, i.e. N,O-dimethacryloylhydroxylamine, which is a new compound prepared according to Czechoslovak Patent Application no. PV 7222-89. N,O-dimethacryloylhydroxylamine is a white crystalline substance with melting point 56° to 58° C., molecular weight $M_z = 169$ determined by mass spectrometry and IR spectrum (KBr pellet) 1770 (C=O ester), 1665 (C=O amide), 1095 (C—O) and 1625 cm$^{-1}$ (CH$_2$—C), which is soluble in ether, methanol and chloroform and insoluble in water. It can be prepared by the reaction of methacryloyl chloride with hydroxylamine hydrochloride dissolved in pyridine at 45° C.

The hydrophilic gels according to the invention are stable in an acid medium at pH 1 to 6.5. In a neutral or weak alkaline medium at pH above 6.5, they undergo degradation as far as to the complete dissolution of the originally insoluble hydrophilic gel.

The appended drawings illustrate solubility of polymers according to the invention as a function of time at various pH values.

FIG. 1 shows the time dependence of percent of the cleaved hydrophilic gel prepared according to example 2 at different values of pH: curve 1—pH 8.0, curve 2—pH 7.4, curve 3—pH 6.5.

Figure 2:
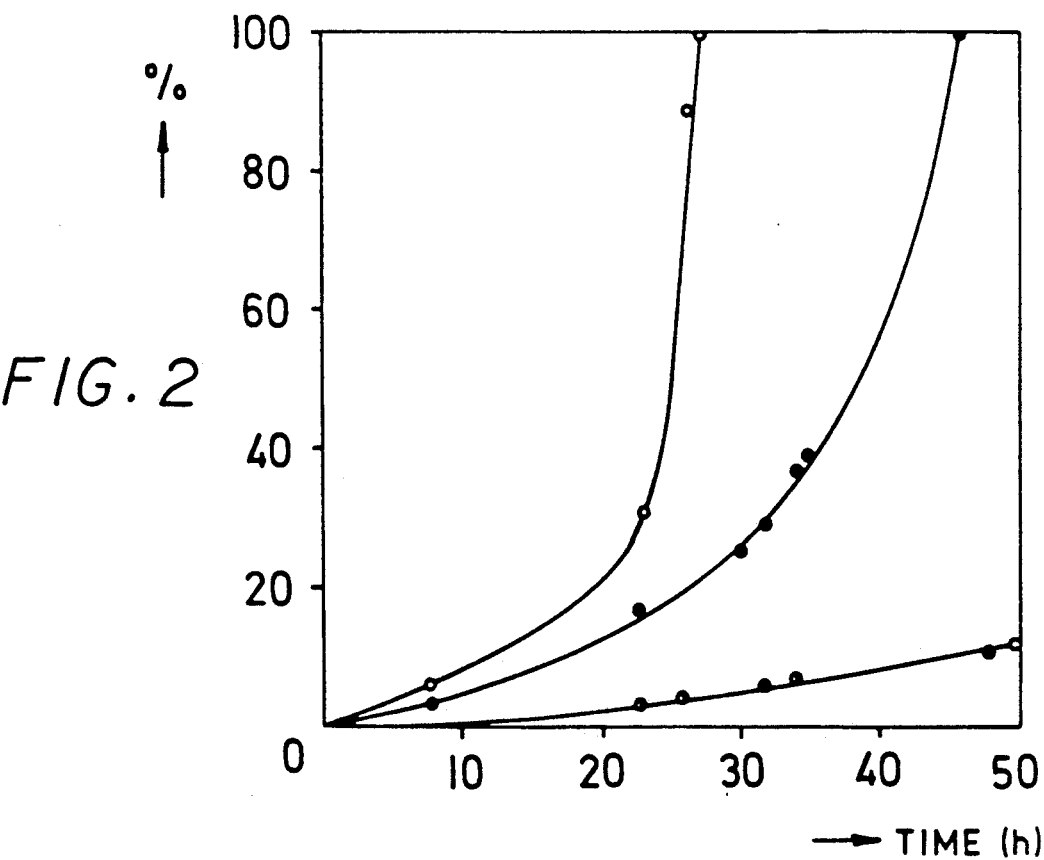

FIG. 2 shows the time dependence of the cleaved hydrophilic gel prepared according to example 3 at different values of pH: curve 1—pH 8.0, curve 2—pH 7.4, curve 3—pH 6.5.

The periods of time required for the total hydrolysis of gels prepared according to examples 2-10 are presented in Table 1. Standard dimensions of disk-shaped samples were diameter 1 cm and thickness 2 mm. The cleavage was carried out at 37° C. in phosphate buffer solution (0.15M) at pH 7.4.

TABLE 1

| Gel according to | 2 | 3 | 4 | 5 | 6 | 7 | 8 | 9 | 10 |
| --- | --- | --- | --- | --- | --- | --- | --- | --- | --- |

TABLE 1-continued

| example. | | | | | | | | | |
|---|---|---|---|---|---|---|---|---|---|
| Time of dissolution, h | 21 | 45 | 18 | 72 | 60 | 120 | 65 | 30 | 55 |

The invention is further illustrated in the examples of performance, without limiting the scope of invention only to them.

EXAMPLE 1

Preparation of N,O-dimethacryloylhydroxylamine

N,O-dimethacryloylhydroxylamine was prepared by the reaction of hydroxylamine with methacryloyl chloride in pyridine medium. Hydroxylamine hydrochloride (10 g; 0.144 mol) was dissolved in 50 ml pyridine (0.632 mol) and 25.4 g (0.243 mol) methacryloyl chloride was dropwise added. Temperature of the reaction mixture was kept below 45° C. After completed addition of methacryloyl chloride, the mixture was stirred at ambient temperature for 2 hours. Then, the mixture was diluted with 100 ml chloroform and 21 ml hydrochloric acid (0.245 mol) was slowly dropwise added in order to transfer pyridine to its hydrochloride. The organic layer was separated, washed four times with 100 ml water, and then dried over $MgSO_4$. Chloroform was evaporated in vacuum and the oily residue was dried in vacuum of an oil pump. The product crystallized during drying, the crystals were filtered and twice recrystallized from the mixture diethyl ether-light petroleum. The yield was 7.0 g (34%) N,O-dimethacryloylhydroxylamine, m.p. 55° C., elemental analysis: calculated C—56.70, H—6.55, N—8.28%; found C—56.74, H—6.22, N—8.34%.

EXAMPLE 2

The hydrophilic polymeric gel was prepared by solution radical polymerization in dimethylsulfoxide. The polymerization was carried out in a mold consisting of two heated plates which were provided with a separation layer from polypropylene. The thickness of hydrophilic polymeric gel was controlled by the thickness of a distance insert from silicon rubber placed between the heated plates.

The polymerization mixture consisted of 3.0 g N-(2-hydroxypropyl)methacrylamide, 0.036 g N,O-dimethacryloylhydroxylamine and 0.060 g azo-bis-isobutyronitrile dissolved in 10 ml dimethylsulfoxide. The solution was bubbled through with nitrogen and then injected into the mold heated to 50° C., where the polymerization was carried out for 24 hours. Disks with diameter of 1.5 cm were cut from the gel and then conditioned in 200 ml methanol for 24 hours. Next day, the gels were allowed to swell in distilled water for 24 hours.

EXAMPLE 3

The hydrophilic polymeric gel based on N-(2-hydroxypropyl)methacrylamide was prepared in the same way as in example 2 with the distinction that 0.073 g N,O-dimethacryloylhydroxylamine was used in the polymerization mixture.

EXAMPLE 4

The hydrophilic polymeric gel based on N-vinylpyrrolidone was prepared in the same way as in example 2. The mixture for polymerization had the following composition: 3.0 g N-vinylpyrrolidone, 0.093 g N,O-dimethacryloylhydroxylamine, 0.132 g azo-bis-isobutyronitrile, 10 ml dimethylsulfoxide.

EXAMPLE 5

The hydrophilic polymer gel based on N,N-diethylacrylamide was prepared in the same way as it is described in example 2 with the distinction that a polypropylene tube with inner diameter 1.5 mm was used as the polymerization mold. The mixture for polymerization had the following composition: 3.0 g N,N-diethylacrylamide, 0.039 g N,O-dimethacryloylhydroxylamine, 0.142 g azo-bis-isobutyronitrile, 10 ml dimethylsulfoxide.

EXAMPLE 6

The hydrophilic polymeric gel based on the copolymer of N-(2-hydroxypropyl)methacrylamide, methacrylic acid and dimethylaminoethyl methacrylate was prepared in the same way as it is described in example 2. The mixture for polymerization had the following composition: 2.0 g N-(2-hydroxypropyl)methacrylamide, 0.41 g methacrylic acid, 0.73 g dimethylaminoethyl, 0.04 g N,O-dimethacryloylhydroxylamine, 0.09 g azo-bis-isobutyronitrile and 5.0 ml dimethylsulfoxide.

EXAMPLE 7

The hydrophilic polymeric gel based on the copolymer vinylpyrrolidone-maleic anhydride was prepared in the same way as it is described in example 2. The mixture for polymerization had the following composition: 1.5 g N-vinylpyrrolidone, 1.3 g maleic anhydride, 0.093 g N,O-dimethacryloylhydroxylamine, 0.132 g azo-bis-isobutyronitrile, and 10 ml dimethylsulfoxide.

EXAMPLE 8

The hydrophilic polymeric gel based on the copolymer of N-(2-hydroxypropyl)methacrylamide with n-butyl methacrylate was prepared by the method described in example 2. The mixture for polymerization had the following composition: 2.1 g N-(2-hydroxypropyl)methacrylamide, 0.9 g n-butyl methacrylate, 0.111 g N,O-dimethacryloylhydroxylamine, 0.143 g azo-bis-isobutyronitrile and 10 ml dimethylformamide.

EXAMPLE 9

N-(2-hydroxypropyl)methacrylamide (5 g) and 0.375 ml dimethylsulfoxide solution containing 0.15 g N,O-dimethacryloylhydroxylamine was dissolved in 6.625 ml water and polymerized by the red-ox initiation system consisting of 1.5 ml water solution containing 0.45 g $(NH_4)_2S_2O_3$ and 1.5 ml water solution containing 0.348 g ascorbic acid. The polymerization was carried out at 30° C. for 4 hours.

EXAMPLE 10

The hydrophilic polymeric gel based on the copolymer acrylic acid-n-butyl acrylate was prepared by the method described in example 2. The mixture for polymerization had the following composition: 1.8 g methacrylic acid, 0.3 g n-butyl acrylate, 40 mg N,O-dimethacryloylhydroxylamine, 20 mg azo-bis-isobutyronitrile and 4 ml dimethylsulfoxide.

The described hydrophilic gels may be used in the preparation of controlled drug release systems, i.e. systems making possible the controlled release of biologically active compounds—drugs from the polymeric matrix (disk, plug, microparticle). The rate of drug release can be controlled by diffusion, rate of gel biodegradation or by the combination of both processes. The drug may be free dispersed in the gel or trapped by means of an ionic or covalent biodegradable bond. Such hydrophilic gels can be advantageously used in the treatment of tumour diseases. After the surgical removal of tumour, the gel containing cancerostatics, e.g. adriamycin, is implanted in the place of intervention. The implanted gel is subjected to hydrolysis in the physiologic environment of the organism (pH 7.4), the cancerostatic is released only on the spot of its required action, the very polymeric matrix is dissolved and the soluble polymer formed is excreted from the organism, e.g., in urine. The whole process is controlled by the rate of biodegradation of the implanted gel.

The described gels may be applied analogously as matrices for the controlled release of various other medicines, e.g., hormones, antibiotics, immunomodulators, etc. A very advantageous application of these gels seems to be the preparation of oral delivery drugs. The matrix with drug is stable in the acid medium (i.e. in stomach) and its degradation with the release of drug can occur first in the environment with higher pH, i.e. in duodenum and intestine.

FIG. 1—% ... time (h)
FIG. 2—% ... time (h)

We claim:

1. Hydrolytically degradable hydrophilic gels comprising cross-linked chains of hydrophilic polymers, wherein said gels are made using N,O-dimethacryloylhydroxylamine as a cross-linking agent.

2. A method for the preparation of hydrolytically degradable hydrophilic gels comprising cross-linked chains of hydrophilic polymers, said method comprising polymerizing a mixture containing one or more hydrophilic monomers and N,O-dimethacryloylhydroxylamine.

3. The method according to claim 2, wherein said hydrophilic monomers are present in said mixture in an amount from about 50 percent to about 99.8 percent by moles of all monomers present.

4. The method according to claim 2, wherein a solvent is present in said mixture.

5. The method according to claim 2, wherein said hydrophilic monomers are chosen from the group consisting of N-(2-hydroxypropyl)methacrylamide, N-isopropylacrylamide, N,N-diethylacrylamide, N-ethylacrylamide, vinylpyrrolidone, maleic anhydride, 2-hydroxyethyl methacrylate, 2-(2-hydroxyethoxy)ethyl methacrylate, acrylic acid, and methacrylic acid.

6. The method according to claim 4, wherein said solvent is chosen from the group consisting of dimethylsulfoxide, dimethylformamide, lower alcohols, water-alcohol mixtures, and water.

7. The method according to claim 3, wherein said mixture contains one or more hydrophobic monomers.

8. The method according to claim 7, wherein said mixture contains a solvent.

9. The method according to claim 7, wherein said hydrophobic monomers are selected from the group consisting of dimethylaminoethyl methacrylate, n-butylmethacrylate, n-butyl acrylate, 2-acetoxyethyl methacrylate, tert-butylacrylamide, methyl methacrylate, and hexyl methacrylate.

* * * * *